US00PP16298P2

(12) United States Plant Patent
Gilford et al.

(10) Patent No.: US PP16,298 P2
(45) Date of Patent: Feb. 28, 2006

(54) STRAWBERRY PLANT NAMED 'DRISCOLL SANIBEL'

(50) Latin Name: *Fragaria×ananassa*
Varietal Denomination: Driscoll Sanibel

(76) Inventors: Kristie L. Gilford, 1525 N. Dover Rd., Dover, FL (US) 33527; Bruce D. Mowrey, 266 Webb Rd., Watsonville, CA (US) 95076

( * ) Notice: Subject to any disclaimer, the term of this patent is extended or adjusted under 35 U.S.C. 154(b) by 100 days.

(21) Appl. No.: 10/923,533

(22) Filed: Aug. 19, 2004

(51) Int. Cl.
*A01H 5/00* (2006.01)

(52) U.S. Cl. ..... Plt./209

(58) Field of Classification Search ..... Plt./209
See application file for complete search history.

*Primary Examiner*—Anne Marie Grunberg
*Assistant Examiner*—Annette H Para
(74) *Attorney, Agent, or Firm*—Jones Day

(57) ABSTRACT

This invention relates to a new and distinct variety of strawberry named 'Driscoll Sanibel.' The variety is similar to the varieties 'Biscayne' and 'Key Largo.' The variety is distinguished from 'Biscayne' and 'Key Largo,' in particular, by its smaller number of teeth on the terminal leaflets, longer fruit length, greater number of achenes per berry, greater average fruit yield, flat terminal leaflet margin profile, and moderate resistance to *Verticillium*.

5 Drawing Sheets

1. Latin name of the genus and species of the plant claimed: The variety is botanically identified as *Fragaria× ananassa.*

1.1 Variety denomination: The strawberry variety denomination is 'Driscoll Sanibel'.

2. BACKGROUND OF THE INVENTION

The new variety originated as a result of a controlled cross between the strawberry plants '10D213' (unpatented variety) and '88E94' (unpatented variety) in an ongoing breeding program, and was discovered as a seedling in Hillsborough, Fla. in 1999. The original seedling of the new cultivar was asexually propagated by stolons in a Nursery in Shasta County, Calif. Propagules were transplanted to a controlled breeding plot in Hillsborough County, Fla., where the variety was identified and selected for further evaluation. 'Driscoll Sanibel' was subsequently asexually propagated and underwent further testing in Hillsborough County, Fla. for three years. This propagation and testing has demonstrated that the combination of traits disclosed herein which characterize the new variety are fixed and retained true to type through successive generations of asexual reproduction.

3. SUMMARY OF THE INVENTION

The present invention relates to a new and distinct variety of strawberry named 'Driscoll Sanibel.' The variety is botanically identified as *Fragaria×ananassa.* The new variety is distinguished from other varieties by a number of characteristics as set forth in Tables 1 to 4.

4. COMPARISON TO SIMILAR VARIETIES

The varieties which we believe to be similar to 'Driscoll Sanibel' from those known to us are 'Biscayne' (U.S. Plant Pat. No. 12,186) and 'Key Largo' (U.S. Plant Pat. No. 8,649). There are several characteristics of the new variety that are different from, or not possessed by 'Biscayne' and 'Key Largo'. The new variety has a smaller number of teeth on the terminal leaflets, a longer fruit length, a greater number of achenes per berry, a greater average fruit yield, a flat terminal leaflet margin profile, and a moderate resistance to *Verticillium.*

'Driscoll Sanibel' is distinguished from its maternal parent '10D213' by its larger average berry size, less vigor, and a more open plant canopy. 'Driscoll Sanibel' is distinguished from its paternal parent '88E94' by its larger average berry size, improved shipping ability, and partial everbearing in comparison to the full everbearing of '88E94'.

5. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

6. DESCRIPTION OF THE NEW VARIETY

Figure 1:
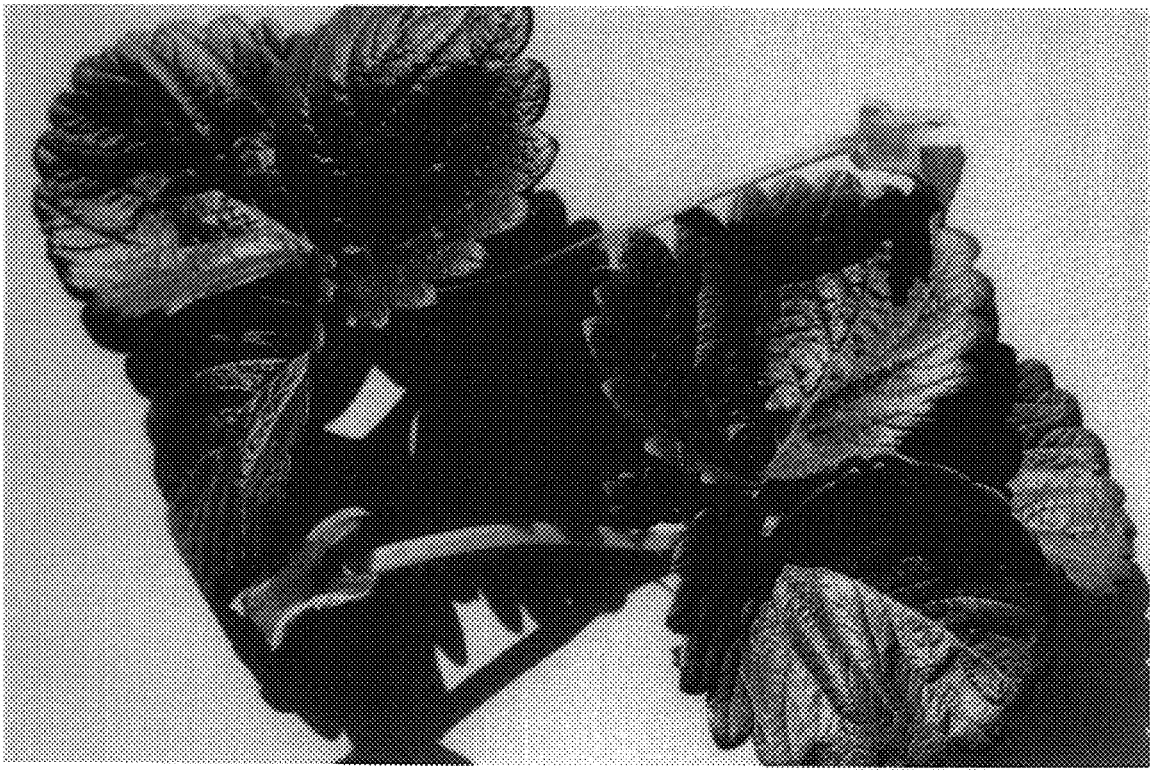
FIG. 1 shows the upper side of the leaves of the plant.
Figure 2:
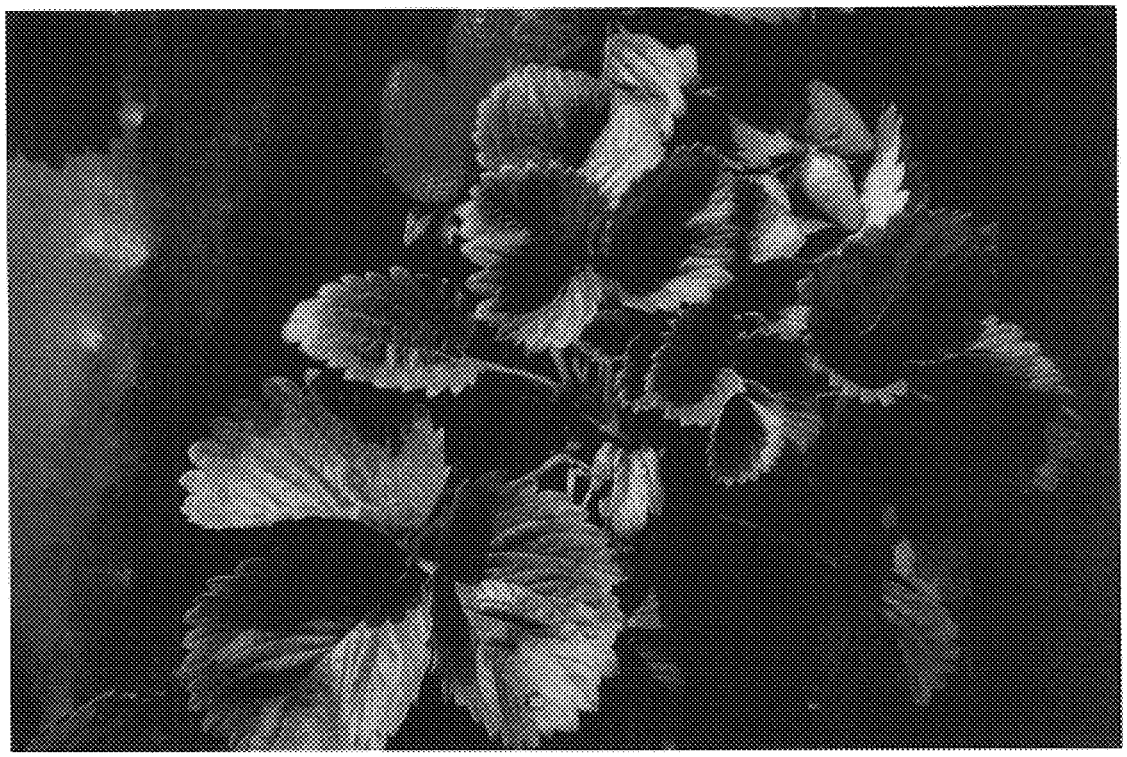
FIG. 2 shows the whole the plant.
Figure 3:
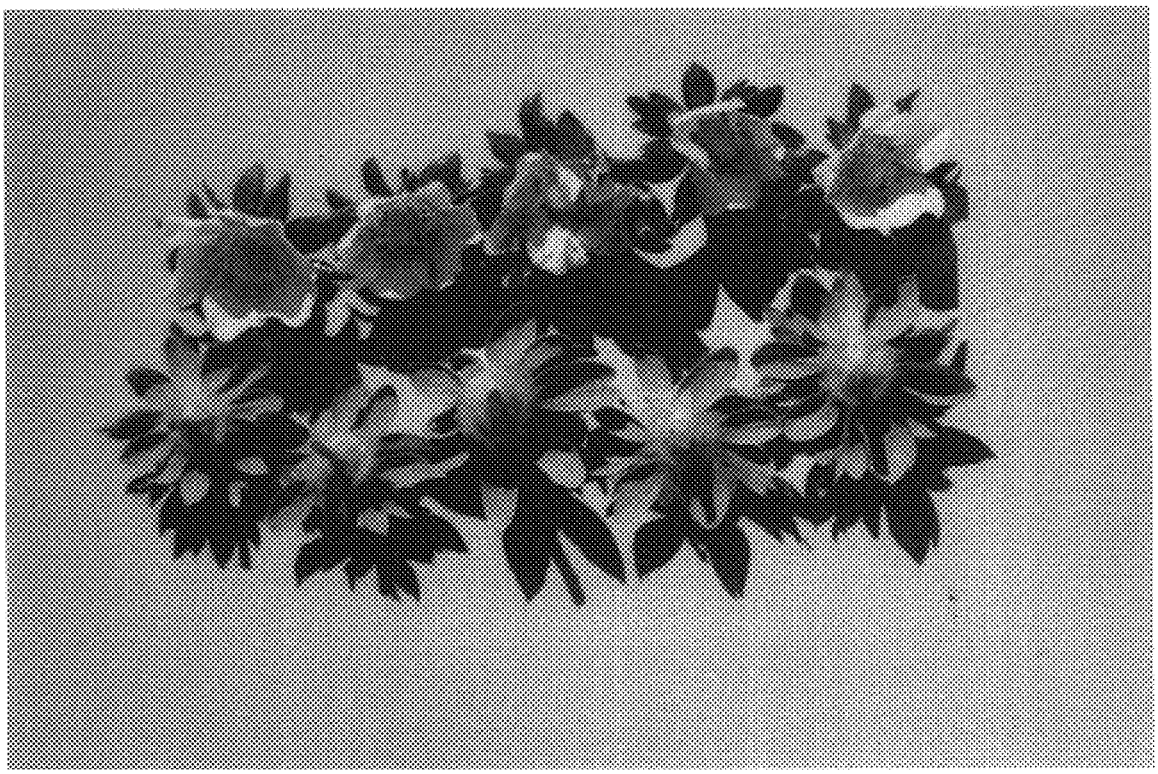
FIG. 3 shows the under side and underside of the flowers.
Figure 4:
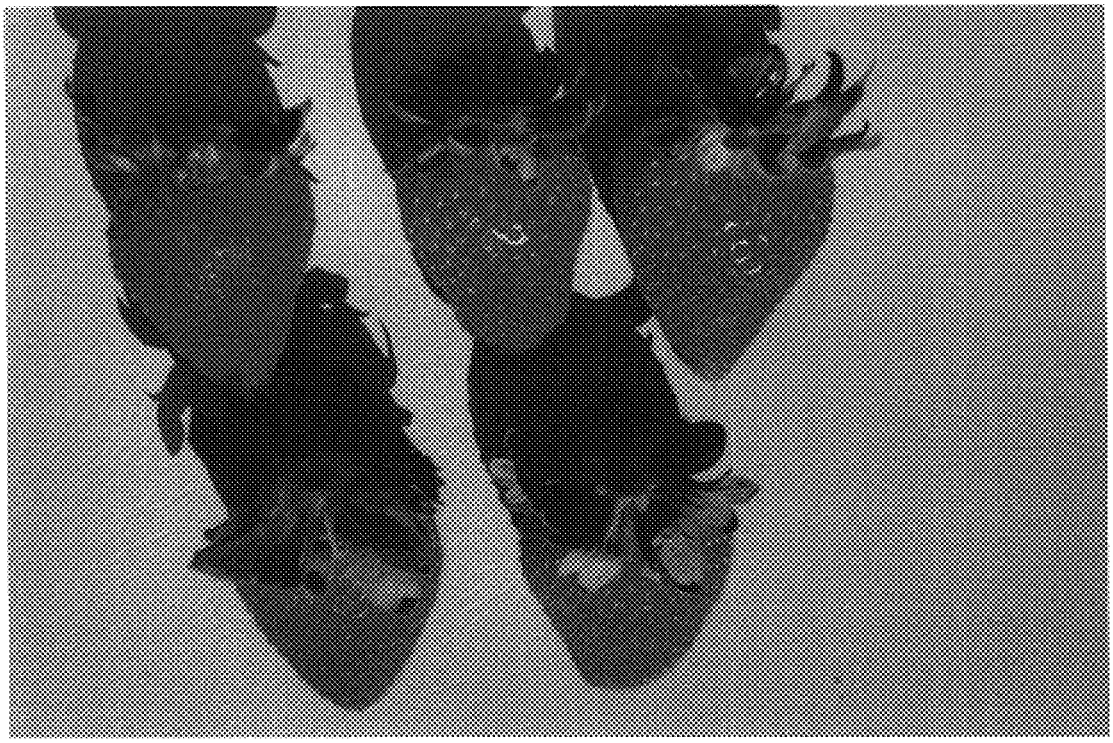
FIG. 4 shows a close-up of the fruit.
Figure 5:
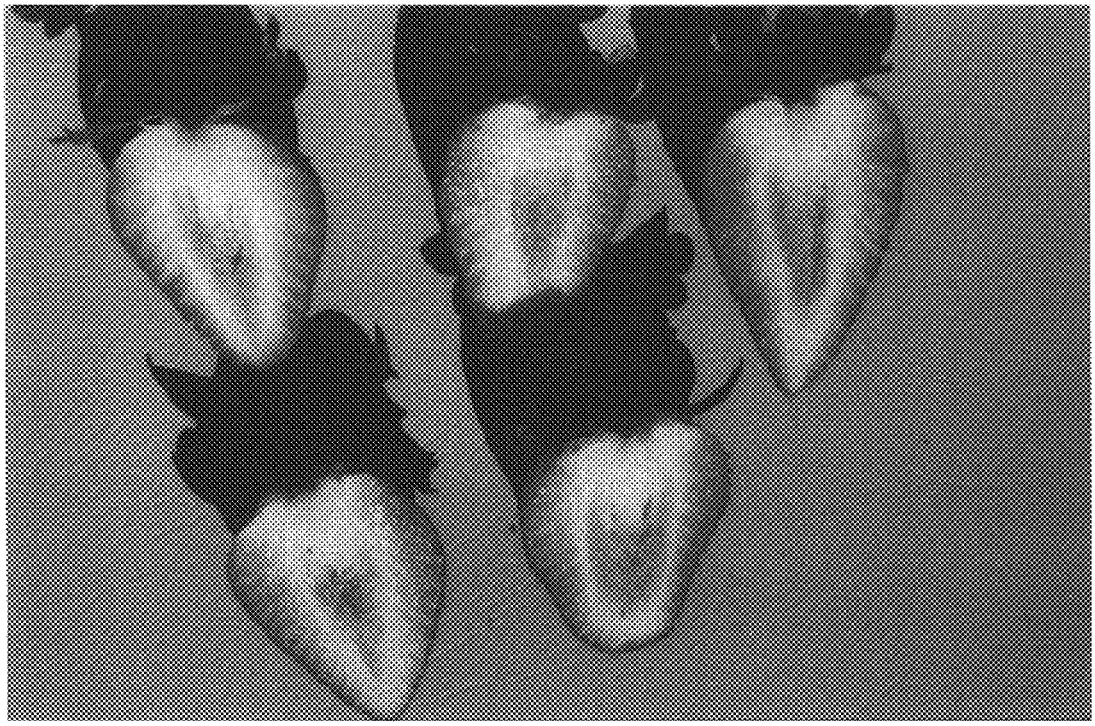
FIG. 5 shows the fruit in longitudinal cross-section.

The following detailed description of the new variety is based upon observations taken of plants and fruit grown in Hillsborough County, Fla., U.S.A. This description is in accordance with UPOV terminology. Observations of 'Driscoll Sanibel', 'Biscayne' and 'Key Largo' were taken in side by side comparison in the 2003–2004 winter season. Plants for observation were harvested from McArthur, Calif., and held in refrigerated storage until planting in Hillsborough county, Fla. in October 2003. Plants were grown in raised beds of soil under conditions typical of commercial strawberry production in central Florida. Fruits were harvested twice weekly for yield determination from November 2003 to March 2004. Measurements of plant, flower, and fruit characteristics were made in January 2004, approximately four months after planting. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

6.1 PROPAGATION

The new variety is principally propagated by way of stolons. Although propagation by stolons is presently preferred, other known methods of propagating strawberry plants may be employed.

6.2 CHARACTERISTICS OF THE NEW VARIETY

Information on the new variety is presented in Tables 1, 2, 3 and 4. In the tables, the flowers described are secondary flowers except where indicated. The fruit described is the secondary fruit on five month old plants. Fruit and flower measurements are an average of both primary and secondary fruit and flowers.

Table 1 provides information on the plant and fruit characteristics of the new variety 'Driscoll Sanibel' compared with characteristics of 'Biscayne' and 'Key Largo.' Table 2 provides additional information of the plant and fruit characteristics of the new variety 'Driscoll Sanibel' compared with characteristics of the varieties 'Biscayne' and 'Key Largo.' Table 3 provides reactions of the new variety to stresses, pests and diseases compared with reactions of the varieties 'Biscayne' and 'Key Largo.' Table 4 provides isozyme characteristics of the new variety as compared to that of the varieties 'Biscayne' and 'Key Largo.'

TABLE 1

QUANTITATIVE COMPARISON OF 'DRISCOLL SANIBEL', 'BISCAYNE,' AND 'KEY LARGO'

| | 'Driscoll Sanibel' | 'Biscayne' | 'Key Largo' |
|---|---|---|---|
| Plant Characteristics | | | |
| Height of Plant (cm) | 13.3 | 10.0 | 11.6 |
| Spread of Plant (cm) | 32.7 | 31.3 | 32.1 |
| Number of Crowns | 3.7 | 3.2 | 4.2 |
| Leaf Characteristics | | | |
| Terminal Leaflet Length (cm) | 7.7 | 7.6 | 8.4 |
| Terminal Leaflet Width (cm) | 8.1 | 8.1 | 8.0 |
| Terminal Leaflet Length/Width Ratio | 0.96 | 0.93 | 1.06 |
| # Teeth/Terminal Leaflet | 19.2 | 27 | 21.6 |
| Color of upper side | 131B medium green | 137A light green | 137A light green |
| Color of under side | 142C light green | 139C light gray green | 139C light gray green |
| Petiole Length (cm) | 11.9 | 9.2 | 11.5 |
| Petiole Color | 145D yellow green | 142D yellow green | 142D yellow green |
| Petiolule Length (mm) | 6.5 | 5.5 | 6.3 |
| Petiolule Diameter (mm) | 2.1 | 2.2 | 1.9 |
| Petiolule Color | 145D yellow green | 142D yellow green | 142D yellow green |

TABLE 1-continued

QUANTITATIVE COMPARISON OF 'DRISCOLL SANIBEL', 'BISCAYNE,' AND 'KEY LARGO'

| | 'Driscoll Sanibel' | 'Biscayne' | 'Key Largo' |
|---|---|---|---|
| Bract Frequency | 25% typically paired | 83% typically paired | 0% |
| Stipule Length (cm) | 3.7 | 3.7 | 3.4 |
| Stipule Width (cm) | 1.8 | 2.0 | 1.5 |
| Stolon Characteristics | | | |
| Anthocyanin color | 53A red | 59B red | |
| Diameter at bract (mm) | 3.21 | 3.24 | 3.30 |
| Avg. # of Daughter plants (2003 Nursery) | 52 | 72 | 52 |
| Flower Characteristics | | | |
| Petal Length (cm) | 1.51 | 1.36 | 1.65 |
| Petal Width (cm) | 1.34 | 1.49 | 1.46 |
| Petal Length/Width Ratio | 1.13 | 0.91 | 1.13 |
| Flower Diameter (cm) | 3.05 | 2.76 | 2.72 |
| Calyx Diameter (cm) | 4.36 | 3.86 | 5.11 |
| Sepal Length (mm) | 17.0 | 15.3 | 21.5 |
| Sepal Width (cm) | 8.0 | 7.22 | 9.15 |
| Petal Color | 155C white | 155C white | 155C white |
| Receptical Color | 149B yellow green | 150A yellow green | 150A yellow green |
| Anther Color | 9A yellow | 9A yellow | 9A yellow |
| Fruiting Truss Length (cm) | 12.9 | 8.7 | 13.6 |
| Fruit Characteristics | | | |
| Fruit Length (cm) | 5.8 | 4.8 | 4.8 |
| Fruit Width (cm) | 4.4 | 4.0 | 3.5 |
| Fruit Length/Width Ratio | 1.31 | 1.20 | 1.37 |
| Average Berry Weight (g) | 32.4 | 26.5 | 23.2 |
| External Color | 43A red | 46B red | 46B red |
| Internal Color | 40C orange red | 44A medium red | 44B medium red |
| Achene Coloration | 182A to 150C greyed red to yellow green | 180B to 150C greyed red to yellow green | 182B to 150A greyed red to yellow green |
| Achenes per berry | 130 | 109 | 104 |
| Achene weight (g) | 0.00077 | 0.00046 | 0.00058 |
| 2003–2004 Fruit Yield (g/plant) | 351 | 243 | 251 |

TABLE 2

QUALITATIVE COMPARISON OF 'DRISCOLL SANIBEL', 'BISCAYNE,' AND 'KEY LARGO'

| | 'Sanibel' | 'Biscayne' | 'Key Largo' |
|---|---|---|---|
| Plant | | | |
| Habit | flat | flat globose | globose |
| Canopy Density | medium | medium | medium |
| Vigor | strong | strong | medium |
| Leaf | | | |
| Shape in cross section | slightly concave | concave | slightly concave |
| Interveinal blistering | medium to strong | weak | weak |
| Glossiness | medium | medium | medium |
| Number of leaflets | three only | three only | three only |

TABLE 2-continued

QUALITATIVE COMPARISON OF 'DRISCOLL SANIBEL', 'BISCAYNE,' AND 'KEY LARGO'

| | 'Sanibel' | 'Biscayne' | 'Key Largo' |
|---|---|---|---|
| Terminal leaflet margin profile | flat | revolute | revolute |
| Terminal leaflet shape of base | obtuse | rounded | slightly oblique |
| Terminal leaflet shape of teeth | rounded | rounded | rounded |
| Stipule pubescence | medium | medium | medium |
| Petiole pubescence | medium | medium | medium |
| Petiole pose of hairs | outward to downward | outwards | upward |
| Stolon | | | |
| Anthocyanin coloration | strong | strong | |
| Thickness | medium | medium | |
| Pubescence | medium | medium | |
| Inflorescence | | | |
| Position relative to foliage | beneath to level with | level | level to above |
| Diameter of calyx relative to corolla on secondary flowers | same size to larger | larger | much larger |
| Diameter of inner calyx relative to outer on secondary flowers | larger | same size | smaller |
| Spacing of petals | touching to overlapping | overlapping | overlapping |
| Fruiting Truss | | | |
| Attitude at first picking | prostrate | prostrate | semi-erect |
| Fruit | | | |
| Predominant shape | conical | conical | conical |
| Difference in shapes between primary and secondary fruits | slight | slight | slight |
| Band without achenes | narrow | narrow | narrow |
| Unevenness of surface | medium | weak | weak |
| Evenness of color | even | even | even |
| Glossiness | strong | strong | strong |
| Insertion of achenes | level with surface | level with surface | below surface |
| Insertion of calyx | level | level | set above |
| Pose of the calyx segments | spreading to reflexed | spreading | reflexed |
| Size of calyx in relation to fruit on secondary fruit | larger | larger | larger |
| Adherence of calyx | strong | strong | strong |
| Firmness of flesh | medium | firm | firm |
| Evenness of flesh color | slightly uneven | slightly uneven | slightly uneven |
| Distribution of flesh color | marginal and central | marginal and central | marginal and central |
| Hollow center size | medium | large | medium |
| Sweetness | strong | strong | medium |
| Texture when tasted | fine | fine | medium |
| Acidity | medium | medium | medium |
| Time of First Flowering in 2003–2004 | Early November | Mid-November | Late November |
| Harvest Interval in 2003–2004 | Late November to Mid-March | Early December to Mid-March | Late December to Mid-March |
| Type of Bearing | partially everbearing | partially everbearing | partially everbearing |

6.3 REACTION TO STRESS, PESTS, AND DISEASE

TABLE 3

REACTIONS TO STRESS PESTS AND DISEASES FOR 'DRISCOLL SANIBEL', 'BISCAYNE,' AND 'KEY LARGO'

| | 'Driscoll Sanibel' | 'Biscayne' | 'Key Largo' |
|---|---|---|---|
| Reaction to Pests | | | |
| *Tetranychus urticae* | susceptible | susceptible | moderately susceptible |
| *Lygus hesperus* | susceptible | susceptible | susceptible |
| Reaction To Diseases | | | |
| Botrytis fruit rot | susceptible | susceptible | susceptible |
| Powdery mildew | susceptible | moderately susceptible | susceptible |
| *Verticillium* wilt | susceptible | susceptible | susceptible |
| Strawberry Mottle Virus | moderately resistant | moderately resistant | moderately resistant |
| *Xanthomonas fragariae* | moderately susceptible | moderately susceptible | moderately susceptible |

6.4 ISOZYME ANALYSIS

In addition to the morphological description above, the new cultivar 'Driscoll Sanibel' has been analyzed to obtain an indication of its genetic makeup to provide further means for identifying the new variety and distinguishing it from other somewhat similar and/or related strawberry varieties. Specifically, leaf samples of 'Driscoll Sanibel', 'Biscayne' and 'Key Largo' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL SANIBEL', 'BISCAYNE,' AND 'KEY LARGO'

| Locus | 'Driscoll Sanibel' | 'Biscayne' | 'Key Largo' |
|---|---|---|---|
| PGI | A1 | A1 | A1 |
| LAP | B3 | B3 | B3 |
| PGM | C2 | C4 | C4 |

What is claimed:

1. A new and distinct variety of strawberry plant, substantially as shown and described.

* * * * *